United States Patent
Hess et al.

(10) Patent No.: US 10,335,196 B2
(45) Date of Patent: Jul. 2, 2019

(54) SURGICAL INSTRUMENT HAVING A STOP GUARD

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Monica L. Zeckel, Cincinnati, OH (US); Jeffrey L. Savage, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 537 days.

(21) Appl. No.: 14/840,691

(22) Filed: Aug. 31, 2015

(65) Prior Publication Data
US 2017/0056068 A1    Mar. 2, 2017

(51) Int. Cl.
A61B 17/34    (2006.01)
A61B 17/32    (2006.01)
(Continued)

(52) U.S. Cl.
CPC .......... *A61B 17/3496* (2013.01); *A61B 17/29* (2013.01); *A61B 17/320016* (2013.01);
(Continued)

(58) Field of Classification Search
CPC .................... A61B 17/3496; A61B 17/320016
(Continued)

(56) References Cited

U.S. PATENT DOCUMENTS

| 3,043,309 A | 7/1962 | McCarthy |
| 3,358,676 A | 12/1967 | Frei et al. |

(Continued)

FOREIGN PATENT DOCUMENTS

| DE | 101 49 421 A1 | 4/2003 |
| EP | 1 709 900 A1 | 10/2006 |

(Continued)

OTHER PUBLICATIONS

International Search Report dated Mar. 21, 2011; International Application No. PCT/US2010/051812 (7 pages).

(Continued)

*Primary Examiner* — Vy Q Bui
(74) *Attorney, Agent, or Firm* — Mintz Levin Cohn Ferris Glovsky and Popeo, P.C.

(57) ABSTRACT

Surgical instruments and methods including a stop guard are described herein. An exemplary instrument can include an inner shaft disposed within an outer shaft, the inner shaft including a tissue-piercing tip and being effective to secure an end effector to the device. A stop guard can be coupled to the inner shaft and extend through outer shaft sidewall openings when the tip is advanced distally or retract into the outer shaft when the tip is retracted proximally. In a percutaneous procedure, external force applied to the stop guard by the tissue can retract the tip to prevent damage to surrounding tissue as the instrument is advanced distally. Moreover, once passed through pierced tissue, the stop guard can be redeployed when the inner shaft is advanced distally to secure an end effector to the instrument and can prevent inadvertent withdrawal of the instrument.

17 Claims, 10 Drawing Sheets

(51) Int. Cl.
*A61B 17/29* (2006.01)
*A61B 90/00* (2016.01)

(52) U.S. Cl.
CPC ..... *A61B 17/3494* (2013.01); *A61B 2090/034* (2016.02); *A61B 2090/036* (2016.02)

(58) Field of Classification Search
USPC .............. 606/1, 33, 181, 182, 185, 205, 206
See application file for complete search history.

(56) References Cited

U.S. PATENT DOCUMENTS

| | | |
|---|---|---|
| 3,710,399 A | 1/1973 | Hurst |
| 3,893,448 A | 7/1975 | Brantigan |
| 3,906,217 A | 9/1975 | Lackore |
| 3,988,535 A | 10/1976 | Hickman et al. |
| 4,047,136 A | 9/1977 | Satto |
| 4,063,561 A | 12/1977 | McKenna |
| 4,099,192 A | 7/1978 | Aizawa et al. |
| 4,278,077 A | 7/1981 | Mizumoto |
| 4,384,584 A | 5/1983 | Chen |
| 4,585,282 A | 4/1986 | Bosley |
| 4,597,390 A | 7/1986 | Mulhollan et al. |
| 4,655,746 A | 4/1987 | Daniels et al. |
| 5,052,402 A | 10/1991 | Bencini et al. |
| 5,201,743 A | 4/1993 | Haber et al. |
| 5,282,806 A | 2/1994 | Haber et al. |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpern et al. |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,540,648 A | 7/1996 | Yoon |
| 5,562,655 A | 10/1996 | Mittelstadt et al. |
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,716,326 A | 2/1998 | Dannan |
| 5,762,255 A | 6/1998 | Chrisman et al. |
| 5,792,165 A | 8/1998 | Klieman et al. |
| 5,810,877 A | 9/1998 | Roth et al. |
| 5,881,615 A | 3/1999 | Dahl et al. |
| 5,928,263 A | 7/1999 | Hoogeboom |
| 5,980,455 A | 11/1999 | Daniel et al. |
| 6,024,748 A | 2/2000 | Manzo et al. |
| 6,059,719 A | 5/2000 | Yamamoto et al. |
| 6,099,537 A | 8/2000 | Sugai et al. |
| 6,159,200 A | 12/2000 | Verdura et al. |
| 6,309,397 B1 | 10/2001 | Julian et al. |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,083,579 B2 | 8/2006 | Yokoi et al. |
| 7,122,028 B2 | 10/2006 | Looper et al. |
| 7,125,403 B2 | 10/2006 | Julian et al. |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 | 2/2010 | Abou El Kheir |
| 7,678,043 B2 | 3/2010 | Gilad |
| 7,691,103 B2 | 4/2010 | Fernandez et al. |
| 7,691,126 B2 | 4/2010 | Bacher |
| 7,699,835 B2 | 4/2010 | Lee et al. |
| 7,722,599 B2 | 5/2010 | Julian et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,128,643 B2 | 3/2012 | Aranyi et al. |
| 8,182,414 B2 | 5/2012 | Handa et al. |
| 8,187,166 B2 | 5/2012 | Kuth et al. |
| 8,372,105 B2 * | 2/2013 | Nishiuchi .......... A61B 5/15142 606/181 |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,623,011 B2 | 1/2014 | Spivey |
| 8,636,648 B2 | 1/2014 | Gazdzinski |
| 8,721,539 B2 | 5/2014 | Shohat et al. |
| 8,764,735 B2 | 7/2014 | Coe et al. |
| 8,845,661 B2 | 9/2014 | D'Arcangelo et al. |
| 9,142,527 B2 | 9/2015 | Lee et al. |
| 9,282,879 B2 | 3/2016 | Farin et al. |
| 9,308,011 B2 | 4/2016 | Chao et al. |
| 9,408,628 B2 | 8/2016 | Altamirano |
| 9,451,937 B2 | 9/2016 | Parihar |
| 2001/0051766 A1 | 12/2001 | Gazdzinski |
| 2003/0060702 A1 | 3/2003 | Kuth et al. |
| 2003/0114731 A1 | 6/2003 | Cadeddu et al. |
| 2004/0093039 A1 | 5/2004 | Schumert |
| 2004/0133235 A1 | 7/2004 | Bacher |
| 2004/0152941 A1 | 8/2004 | Asmus et al. |
| 2005/0033354 A1 | 2/2005 | Montalvo et al. |
| 2005/0070758 A1 | 3/2005 | Wells et al. |
| 2005/0085697 A1 | 4/2005 | Yokoi et al. |
| 2005/0119640 A1 | 6/2005 | Sverduk et al. |
| 2005/0131396 A1 | 6/2005 | Stanczak et al. |
| 2005/0165449 A1 | 7/2005 | Cadeddu et al. |
| 2005/0215983 A1 | 9/2005 | Brock |
| 2005/0250984 A1 | 11/2005 | Lam et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0149135 A1 | 7/2006 | Paz |
| 2006/0184161 A1 | 8/2006 | Maahs et al. |
| 2006/0190035 A1 | 8/2006 | Hushka et al. |
| 2006/0195015 A1 | 8/2006 | Mullick et al. |
| 2006/0229592 A1 | 10/2006 | Yokoi et al. |
| 2006/0258905 A1 | 11/2006 | Kaji et al. |
| 2007/0010709 A1 | 1/2007 | Reinschke |
| 2007/0049966 A1 | 3/2007 | Bonadio et al. |

(56) References Cited

U.S. PATENT DOCUMENTS

| | | |
|---|---|---|
| 2007/0073247 A1 | 3/2007 | Ewaschuk |
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0299387 A1 | 12/2007 | Williams et al. |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0209947 A1 | 8/2009 | Gordin et al. |
| 2010/0063538 A1 | 3/2010 | Spivey et al. |
| 2010/0168774 A1* | 7/2010 | Morita ............... A61B 5/15142 606/181 |
| 2010/0249700 A1 | 9/2010 | Spivey |
| 2010/0298774 A1 | 11/2010 | Igov |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0115891 A1 | 5/2011 | Trusty |
| 2011/0160538 A1* | 6/2011 | Ravikumar ...... A61B 17/00234 600/204 |
| 2011/0208007 A1 | 8/2011 | Shohat et al. |
| 2011/0230869 A1 | 9/2011 | Altamirano |
| 2011/0276057 A1 | 11/2011 | Conlon et al. |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0095298 A1 | 4/2012 | Stefanchik et al. |
| 2012/0259325 A1 | 10/2012 | Houser et al. |
| 2012/0316575 A1 | 12/2012 | Farin et al. |
| 2013/0138091 A1 | 5/2013 | Coe et al. |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1 | 3/2014 | Parihar et al. |
| 2014/0088638 A1 | 3/2014 | Parihar |
| 2014/0243799 A1 | 8/2014 | Parihar |
| 2014/0243800 A1 | 8/2014 | Parihar |
| 2014/0277018 A1 | 9/2014 | Parihar |
| 2014/0378953 A1 | 12/2014 | Coe et al. |
| 2015/0088191 A1 | 3/2015 | Coe et al. |
| 2015/0142049 A1 | 5/2015 | Delgado et al. |
| 2017/0055970 A1 | 3/2017 | Hess et al. |

FOREIGN PATENT DOCUMENTS

| | | |
|---|---|---|
| JP | 2005-261734 A | 9/2005 |
| JP | 2008-518716 A | 6/2008 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/081702 A1 | 7/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |
| WO | 2015047886 A1 | 4/2015 |

OTHER PUBLICATIONS

International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCTMS2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
US Application as filed on Oct. 9, 2009 for U.S. Appl. No. 12/576,529 (18 pages).
International Search Report and Written Opinion for Application No. PCT/US2016/049011 dated Oct. 17, 2016.

* cited by examiner

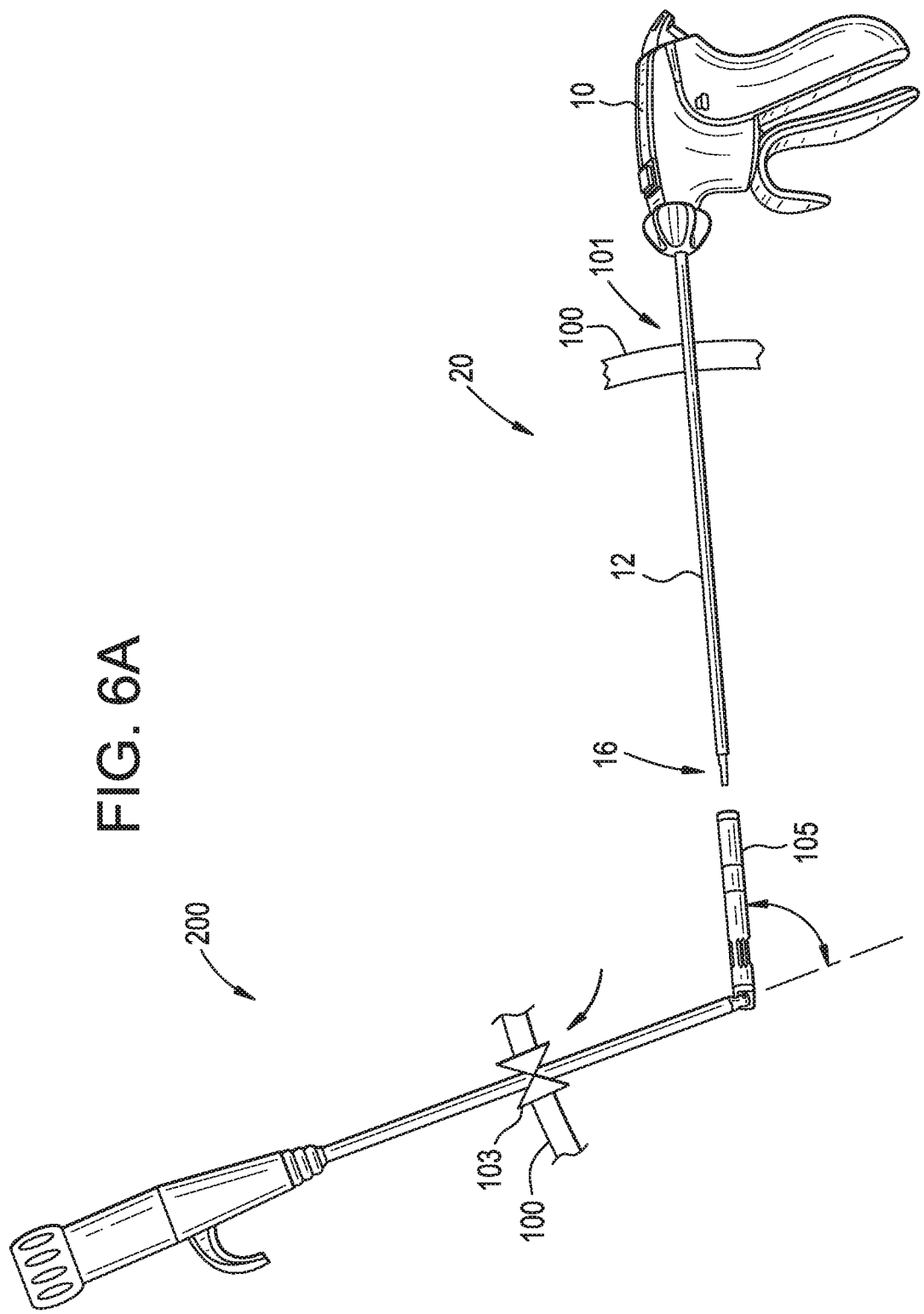

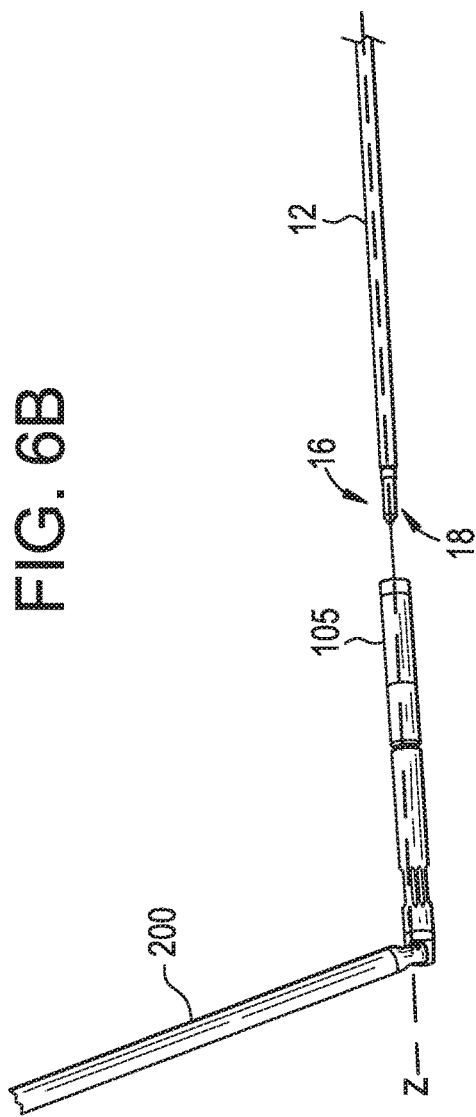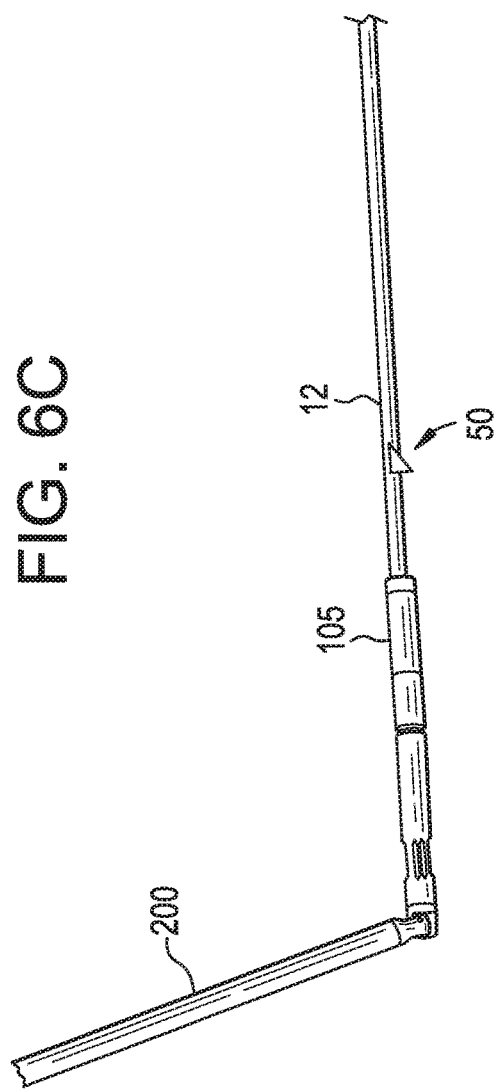

SURGICAL INSTRUMENT HAVING A STOP GUARD

FIELD OF INVENTION

This disclosure relates generally to surgical instruments and, more particularly, to such instruments that include a stop guard for preventing over-insertion into, and inadvertent removal from, a patient's body.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures.

Minimally invasive surgery can have numerous advantages compared to traditional open surgery, including reduced recovery time, pain, and surgery-related complications. In many minimally invasive procedures, the abdominal cavity is insufflated with carbon dioxide gas to provide adequate space to perform the procedure. The insufflated cavity is generally under pressure and is sometimes referred to as being in a state of pneumoperitoneum. Surgical access devices are often used to facilitate surgical manipulation of internal tissue while maintaining pneumoperitoneum. For example, during a surgical procedure, the abdominal wall can be pierced and a cannula or trocar can be inserted into the abdominal cavity. Surgeons can then perform a variety of procedures while minimizing patient trauma.

Various surgical instruments can be configured to manipulate tissue during a minimally invasive surgical procedure. An exemplary surgical instrument can include an actuator and an elongate shaft with an end effector that can be selectively coupled to the shaft and can articulate relative to the shaft. Such a device can include one or more modular features, such as an end effector that can be selectively attached to, and detached from, the shaft using a locking mechanism. The device can also include an inner shaft disposed within the elongate shaft, and the inner shaft can include a pointed tip for piercing the abdominal wall. Accordingly, the device can be inserted into a patient's body without an end effector attached by using the pointed tip of the inner shaft to form an incision in tissue. The end effector can then be selectively attached to the patient within, e.g., the abdominal cavity, to perform the procedure.

While the pointed tip of the instrument can be useful for piercing the abdominal wall, it can cause damage to surrounding tissue if the instrument is inserted too far into a patient's body. Even if the instrument is not over-inserted distally, moving the pointed tip around within the body can cause undesirable damage to nearby tissue. Furthermore, it is also possible that a user can easily withdraw the surgical device from the patient's body inadvertently, both when an end effector is attached thereto and, especially, when no end effector is attached because of the low profile of the elongate shaft alone.

In addition, surgical devices configured to selectively couple to end effectors within the body can sometimes employ a clevis-like attachment mechanism that includes opposed arms that are radially deflectable to allow insertion into a socket formed on an end effector. The opposed arms of the attachment mechanism can, in some embodiments, be quite small and thin. There is a risk that these arms can become permanently bent or otherwise deformed if, for example, an end effector is not correctly aligned during coupling (e.g., if only one of the arms enters the socket on the end effector while the other arm remains outside the socket, the arms can be bent away from one another). It is also possible that tissue or other nearby structures can catch one of the arms during insertion and/or withdrawal of the device.

Accordingly, there is a need for improved devices and methods that assist users in preventing over-insertion and/or unintentional withdrawal of a device being passed through tissue. There is also a need for devices and methods that protect against damage to an attachment mechanism used to couple to an end effector.

SUMMARY OF THE INVENTION

The present invention generally provides surgical devices and methods that prevent over-insertion and/or unintentional withdrawal of an instrument being passed percutaneously through tissue, while also providing protection to any more delicate components of the device, such as an attachment mechanism. The instruments described herein generally include a selectively deployable stop guard coupled to a pointed distal tip of the instrument. The stop guard can be configured to deploy when the pointed distal tip is exposed to puncture tissue. As the distal tip is advanced through tissue, the deployed stop guard can contact the tissue being punctured and move into a retracted configuration in response to a force exerted on the stop guard by the tissue. This movement can cause the distal tip coupled to the stop guard to also move into a retracted position, preventing any undesired damage to nearby tissue. Moreover, once the stop guard is advanced through the tissue in the retracted configuration, it can again be selectively deployed and utilized to provide increased resistance to removing the instrument from the patient's body.

The instruments described herein can also include features that protect against damage to an attachment mechanism used to couple a distal end of the instrument to an end effector. Such components can include, for example, a protective sheath that can selectively surround a distal portion of the device, as well as a snap ring or other retaining device that can provide support to, for example, opposed arms of a clevis-like attachment mechanism.

In one aspect, a surgical instrument is provided that includes an outer shaft having an inner lumen and at least one sidewall opening formed therein. The instrument can further include an inner shaft disposed within the inner lumen of the outer shaft and configured to translate relative to the outer shaft along a longitudinal axis thereof. The inner shaft can also include a distal end configured to puncture tissue. The instrument can also include a stop guard coupled to the inner shaft and having at least one retractable wing configured to both extend radially outward through the at least one sidewall opening of the outer shaft and retract radially inward towards the inner shaft such that the retractable wing is disposed within a diameter of the outer shaft. Further, when the at least one retractable wing is extending radially outward through the at least one sidewall opening of the outer shaft, the at least one retractable wing can be configured to retract radially inward towards the inner shaft in response to the at least one retractable wing coming into contact with an external object as the instrument is advanced distally into tissue. Moreover, the radially inward retraction of the at least one retractable wing can result in the distal end of the inner shaft retracting proximally towards the distal end of the outer shaft.

The devices and methods described herein can have a number of additional features and/or variations, all of which are within the scope of the present disclosure. In some embodiments, for example, the distal end of the inner shaft can be configured to retract proximally towards the distal end of the outer shaft such that, upon contact with an external object by the at least one retractable wing, the distal end of the inner shaft is disposed within the inner lumen of the outer shaft.

In other embodiments, the instrument can further include an intermediate shaft having an inner lumen and at least one sidewall opening formed therein. The intermediate shaft can be disposed between the outer shaft and the inner shaft and can be configured to translate relative to the outer shaft along a longitudinal axis thereof. The intermediate shaft can be further configured to translate to a position at which the at least one sidewall opening of the intermediate shaft is aligned along at least a portion of its length with the at least one sidewall opening of the outer shaft and a distal end of the intermediate shaft extends distally beyond the distal end of the outer shaft. In such an embodiment, the distal end of the inner shaft can be configured to retract proximally towards the distal end of the intermediate shaft, upon contact with an external object by the at least one retractable wing, such that the distal end of the inner shaft is disposed within the inner lumen of the intermediate shaft.

In certain embodiments, each of the intermediate and outer shafts can include first and second deflectable arms. The deflectable arms can be extended radially outward by the inner shaft moving distally between them, and the radial extension of the arms can secure an end effector to a distal end of, for example, the intermediate and/or outer shafts. Accordingly, in some embodiments the instrument can include an end effector configured to be coupled to at least one of the distal end of the intermediate shaft and the distal end of the outer shaft by the inner shaft extending the first and second deflectable arms of the intermediate shaft and/or the outer shaft radially outward towards sidewalls of the end effector. Moreover, in some embodiments the at least one retractable wing of the stop guard can be configured to extend radially outward through the at least one sidewall opening of the outer shaft when the end effector is coupled to at least one of the distal end of the intermediate shaft and the distal end of the outer shaft.

In embodiments that include an intermediate shaft, the stop guard can have a fully retracted position in which an outer-most radius of the stop guard is greater than a radius of the intermediate shaft but less than a radius of the outer shaft.

The stop guard can have a variety of shapes and configurations. In some embodiments, for example, the at least one retractable wing of the stop guard can include a first retractable wing and a second retractable wing, the first and second retractable wings being configured to extend radially outward through first and second sidewall openings of the at least one sidewall opening of the outer shaft, respectively, and retract radially inward towards the inner shaft such that the first and second retractable wings are disposed within a diameter of the outer shaft. In some embodiments, for example, the first and second retractable wings can be disposed on opposite sides of the inner shaft from one another. In other embodiments, however, a different number of retractable wings can be utilized, and the wings can be positioned differently about the instrument.

In another aspect, a surgical instrument is provided that can include an outer shaft having an inner lumen and at an least one sidewall opening formed therein, as well as an inner shaft disposed within the inner lumen of the outer shaft and configured to translate relative to the outer shaft along a longitudinal axis thereof. The inner shaft also includes a distal end configured to puncture tissue. The instrument further includes a stop guard coupled to the inner shaft and configured to proximally retract the inner shaft upon contact with tissue such that the distal end of the inner shaft is contained within the inner lumen of the outer shaft. Accordingly, the stop guard can effect automatic retraction of the tissue-puncturing distal tip of the inner shaft at a predetermined depth of insertion, e.g., as the instrument passes through tissue, such as the abdomen wall. Further, the retraction can be effected via interaction between the stop guard and the tissue (e.g., an abdomen wall).

As with the instrument described above, a number of variation and additional features are possible. For example, the stop guard can be further configured to move between a first position, in which the stop guard extends through the at least one sidewall opening when the distal end of the inner shaft extends distally beyond a distal end of the outer shaft, and a second position, in which the stop guard is retracted towards the inner shaft such that a radius of the stop guard is less than a radius of the outer shaft when the distal end of the outer shaft is disposed within the inner lumen of the outer shaft.

In other embodiments, the instrument can include an intermediate shaft having an inner lumen and at least one sidewall opening formed therein, the intermediate shaft being disposed between the outer shaft and inner shaft and configured to translate relative to the outer shaft along a longitudinal axis thereof. The intermediate shaft can be further configured to translate to a position at which the at least one sidewall opening of the intermediate shaft is aligned along at least a portion of its length with the at least one sidewall opening of the outer shaft and a distal end of the intermediate shaft extends distally beyond the distal end of the outer shaft.

In certain embodiments, each of the intermediate and outer shafts can include first and second deflectable arms. In such embodiments, the retractable stop guard can be configured to move to a third position, in which the stop guard extends through the at least one sidewall opening of both the intermediate shaft and the outer shaft, and the distal end of the inner shaft is disposed at or distal of the distal end of the intermediate shaft to cause the first and second deflectable arms of the intermediate shaft to extend radially outward towards sidewalls of an end effector to couple the end effector to at least one of the intermediate shaft and the outer shaft.

In another aspect, a method for puncturing tissue is provided that includes passing an inner shaft of an instrument distally through a lumen of an outer shaft of the instrument such that a distal end of the inner shaft extends beyond a distal end of the outer shaft and a stop guard coupled to the inner shaft extends radially outward of the outer shaft. The method can further include forming a puncture in tissue by advancing a distal end of the inner shaft into tissue. The method can also include advancing the instrument through the puncture until the stop guard coupled to the inner shaft and extending radially outward of the outer shaft contacts the tissue in which the puncture was formed, thereby causing the stop guard to retract radially inward toward the inner shaft and the distal end of the inner shaft to retract proximally toward the distal end of the outer shaft. In some embodiments, the distal end of the inner shaft can retract proximally into the lumen of the outer shaft in response to the stop guard retracting radially inward toward the inner shaft.

In other embodiments, the method can further include advancing the instrument through the puncture when the stop guard is retracted radially inward such that the stop guard passes through the puncture, and coupling an end effector to the outer shaft by advancing the distal end of the inner shaft distally through the lumen of the outer shaft such that the stop guard moves from its retracted radially inward position to extending radially outward of the outer shaft.

In certain embodiments, an intermediate shaft having an inner lumen can be disposed between the outer shaft and the inner shaft and can be positioned such that a distal end of the intermediate shaft extends distally beyond the distal end of the outer shaft. Further, passing the inner shaft of the instrument distally through the lumen of the outer shaft can also include passing the inner shaft distally such that the distal end of the inner shaft extends beyond a distal end of the intermediate shaft.

In still other embodiments, the method can further include advancing the instrument through the puncture when the stop guard is retracted radially inward such that the stop guard passes through the puncture. The method can also include coupling an end effector to at least one of the intermediate shaft and the outer shaft by advancing the distal end of the inner shaft distally through the lumen of the intermediate shaft such that the stop guard moves from its retracted radially inward position to extending radially outward of the intermediate shaft.

Any of the features or variations described above can be applied to any particular aspect or embodiment of the invention in a number of different combinations. The absence of explicit recitation of any particular combination is due solely to the avoidance of repetition in this summary.

BRIEF DESCRIPTION OF THE DRAWINGS

FIG. 6A is a side view of one embodiment of a surgical instrument and a loading device prior to coupling an end effector to the surgical instrument;

FIG. 6B is a detail view of the instrument and loading device of FIG. 6A, including a distal mating feature of the instrument being positioned adjacent to, and in axial alignment with, the loading device;

FIG. 6C is a detail view of the instrument and loading device of FIG. 6A, including the instrument coupling to an end effector held by the loading device;

DETAILED DESCRIPTION OF THE INVENTION

Figure 1:
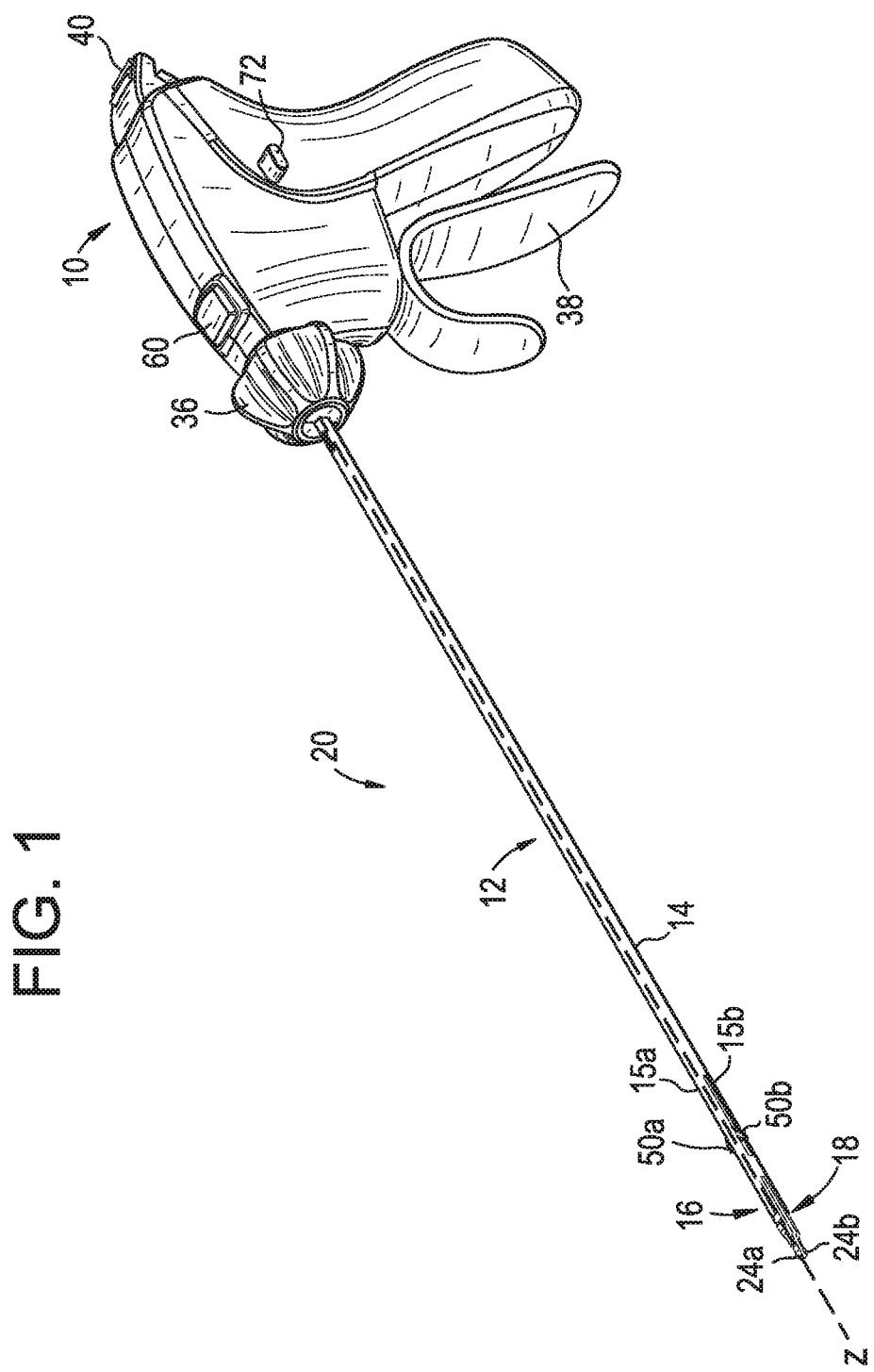
FIG. 1 is a perspective view of one embodiment of a surgical instrument having a stop guard.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

Surgical devices and methods are described herein that include features to prevent over-insertion and/or accidental removal of a device being passed percutaneously into a patient's body. Such devices can generally include an actuator and an elongate shaft that can extend from the actuator, and a distal end of the shaft can be configured to selectively couple to an end effector in vivo or ex vivo. The elongate shaft can itself include an outer shaft, an intermediate shaft, and an inner shaft with a selectively deployable stop guard coupled thereto, as explained in more detail below. In one exemplary embodiment, a device or instrument for performing a surgical procedure can be provided that includes an inner shaft or obturator with a pointed distal tip configured to puncture tissue and a selectively deployable stop guard configured to prevent damage to surrounding tissue as a result of over-insertion of the distal tip. Further, the stop guard can be configured to proximally retract the inner shaft upon contact with tissue (e.g., tissue being penetrated by the instrument) such that the tissue-puncturing distal end of the inner shaft is safely contained within the outer shaft. Still further, the stop guard can be used to prevent accidental withdrawal of the instrument once positioned inside a patient's body, e.g., by passing the stop guard through tissue in a retracted configuration and deploying it inside the abdominal cavity or other area of a patient's body. The stop guard can have a number of different configurations but, in some embodiments, can include two (or some other number of) wings (or other structures) formed on the inner shaft that can be extended radially when the pointed distal tip is exposed from a distal end of the outer and/or intermediate shafts.

In use, such an instrument can be inserted into a patient's body using the pointed tip on the obturator to puncture and penetrate through tissue. Exemplary tissue can include, for example, a patient's abdomen wall. This is only one example of tissue that can be penetrated, however, and the instrument can also be used in combination with any other tissue found in other areas of the body or with other "non-tissue" objects. The stop guard, which can be extended or deployed when the pointed distal tip is exposed, can contact an external object, such as the tissue being punctured, and prevent the pointed distal tip from extending further into tissue where it might cause undesirable damage. Moreover, a force exerted on the stop guard by the tissue or other external object can cause the stop guard and obturator to retract proximally. This proximal movement can shield the obturator distal tip within the intermediate and/or outer shafts and can cause the stop guard to retract radially inward. In some embodiments, the device can then be further inserted into tissue such that the stop guard, in its retracted state, is positioned on a far side of the punctured tissue within a patient's body. The stop guard can then be selectively deployed again, for example in connection with coupling an end effector to a distal end of the intermediate and/or outer shafts. By way of further example, in some embodiments the obturator or inner shaft having a pointed distal tip can also be utilized to lock an end effector onto a distal end of the intermediate and/or outer shafts. As a result, when an end effector is coupled to the instrument inside a patient's body, the obturator can be advanced distally to secure the connection. The distal advancement of the obturator relative to the intermediate and/or outer shafts can result in the deployment of the stop guard inside the abdominal cavity or other area of the body. Deploying the stop guard inside a patient's body in this manner can prevent inadvertent withdrawal of the instrument from the body.

Figure 2:
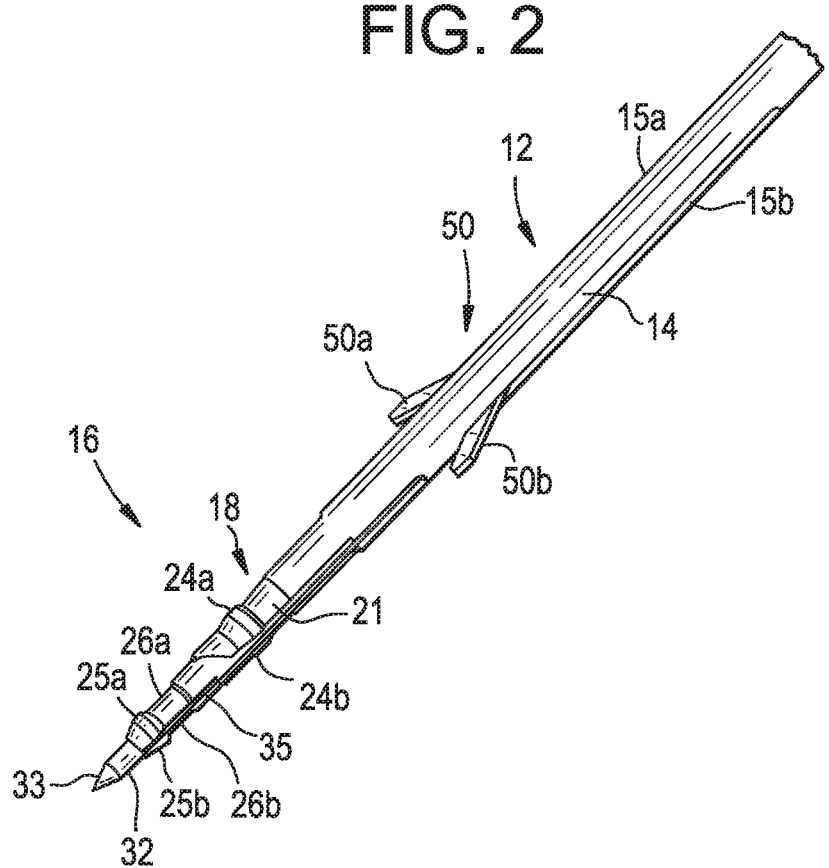
FIG. 2 is a detail view of a distal end of the instrument of FIG. 1.

FIGS. 1-4 illustrate one embodiment of a surgical device or instrument including a selectively deployable stop guard. The device 20 can generally include an actuator 10 and an elongate shaft 12 that can pierce tissue, pass through an incision formed in tissue, and couple to an end effector (see FIG. 6D). The elongate shaft 12 can itself include an outer shaft 14, an inner shaft or obturator 32, and an intermediate shaft 35. As shown in FIG. 2, the inner shaft 32 can include a pointed distal tip 33 that can be configured to pierce tissue. A stop guard 50, such as the one or more wings 50a, 50b, can be coupled to the inner shaft 32 and can be configured to selectively deploy from the outer shaft 14 to serve as an insertion depth stop when the device is advanced distally, as well as a withdrawal stop when the device is retracted proximally. By extending the wings 50a, 50b from the outer shaft 14, the wings can contact tissue being penetrated and a force exerted on the wings by the tissue can cause proximal retraction of the inner shaft 32 relative to the outer shaft 14, thereby preventing over-insertion of a pointed distal tip 33 of the inner shaft 32. Furthermore, if the stop guard 50 is deployed inside a patient's body, for example in connection with coupling an end effector (see FIG. 6D) to the device 20, the wings 50a, 50b can prevent inadvertent withdrawal of the device from a body cavity. The wings 50a, 50b of the stop guard 50 can be selectively deployed through sidewall openings 15a, 15b formed in the outer shaft 14 and the intermediate shaft 35. As shown in the figures, the sidewall openings 15a, 15b can be formed opposite one another in some embodiments (in order to correspond to the placement of the wings 50a, 50b) and can have a length that allows distal and proximal movement of wings that are coupled to the inner shaft 32.

The actuator 10 can include a knob 36 configured to rotate the elongate shaft 12 (and its constituent components) about a longitudinal axis z thereof, which can also result in rotation of any end effector coupled thereto. The actuator 10 can further include a closure actuator, such as a pivotable trigger 38, that is configured to move relative to the actuator 10 to actuate an end effector (e.g., jaws) coupled to the shaft. This can be accomplished, for example, by coupling the pivotable trigger 38 to the intermediate shaft 35, such that movement of the pivotable trigger can cause proximal or distal movement of the intermediate shaft 35 relative to the outer shaft 14. Further, an inner shaft actuator 40, such as a button or a slider, can be configured to control proximal/distal movement of the inner shaft or obturator 32 relative the outer shaft 14. The actuator 10 can also include a lock 72 that can lock the inner shaft 32 in a distally advanced position. The internal actuation components that accomplish the translation of motion of one component, e.g., the pivotable trigger 38, to another, e.g., the intermediate shaft 35, are known to those skilled in the art, thus exact details about every such component is unnecessary (although some further, non-limiting discussion of the same is provided below with respect to FIG. 4). A person skilled in the art will recognize that components associated with the various features of the actuator 10 can be mechanically, electrically, and/or optically-based, and can include various actuators, gears, levers, triggers, and sliders.

Figure 6D:
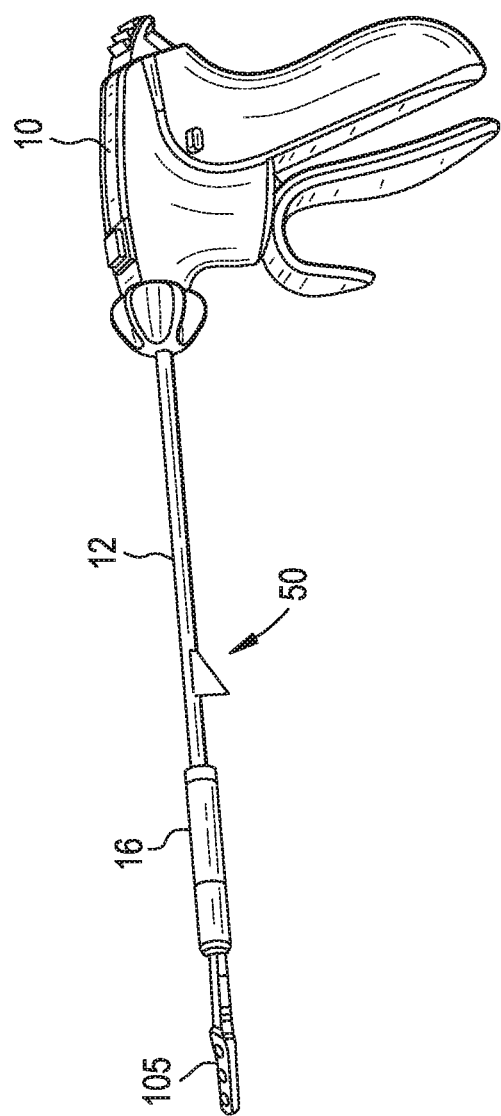
FIG. 6D is a side view of the instrument and loading device of FIG. 6A, including the instrument and end effector coupled thereto pulling away from the loading device.
Figure 6D:
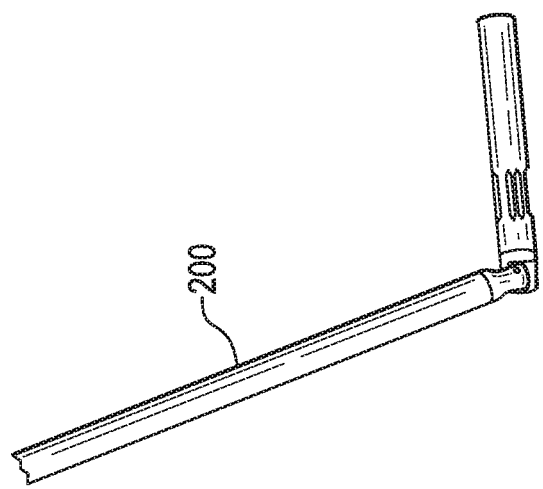

A distal end 16 of the elongate shaft 12 can include an attachment mechanism 18 that can be configured to mate the outer shaft 14 and/or intermediate shaft 35 with a variety of end effectors (e.g., see FIG. 6D). In some embodiments, for example, the outer shaft 14 and/or intermediate shaft 35 can form a clevis-like attachment mechanism 18 that includes opposed arms 24a, 24b of the outer shaft 14 and/or opposed arms 25a, 25b of the intermediate shaft 35. Each of the arms 24a, 24b and 25a, 25b can be radially deflectable to accommodate interfacing with a socket formed in an end effector, as explained in more detail below. Proximal or distal movement of the inner shaft 32 can effectively lock the attachment mechanism 18 because, when the inner shaft 32 is advanced distally (e.g., as shown in FIG. 2), it can occupy the space between the opposed arms 24a, 24b and/or 25a, 25b, thereby preventing any inward radial deflection thereof. Conversely, when refracted proximally (e.g., as shown in FIG. 7C), a gap is present between the opposed arms 24a, 24b and/or 25a, 25b, which can allow inward radial deflection of the arms towards one another.

FIG. 2 illustrates a detailed view of the attachment mechanism 18 located at the distal end 16 of the elongate shaft 12. The attachment mechanism 18 can include a mating feature, such as a circumferential groove 21 located on a lateral surface of outer shaft arms 24a, 24b, that can accommodate a corresponding feature formed on a sidewall of an end effector. As mentioned above, the outer shaft arms 24a, 24b can be resiliently flexible and can include an opening therebetween to allow inward radial deflection towards one another. The attachment mechanism 18 can also include intermediate shaft arms 25a, 25b disposed on the distal end of the intermediate shaft 35 and projecting distally from distal ends of the outer shaft arms 24a, 24b. The intermediate shaft 35, including arms 25a, 25b, can be axially slidable relative to the outer shaft 14, as described above, and can similarly be resiliently deflectable, i.e., flexibly-tensioned, medially (i.e., radially inward) into a gap between the opposed arms. The intermediate shaft arms 25a, 25b can also include one or more mating features, such as stepped lateral notches 26a, 26b, that can be configured to seat corresponding features formed on a socket sidewall of an end effector in order to couple the end effector to the device 20. The inner shaft 32 can be positioned medially relative the intermediate shaft arms 25a, 25b and/or the outer shaft arms 24a, 24b, such that the inner shaft is disposed within an inner lumen of the outer shaft and/or intermediate shaft.

Figure 7A:
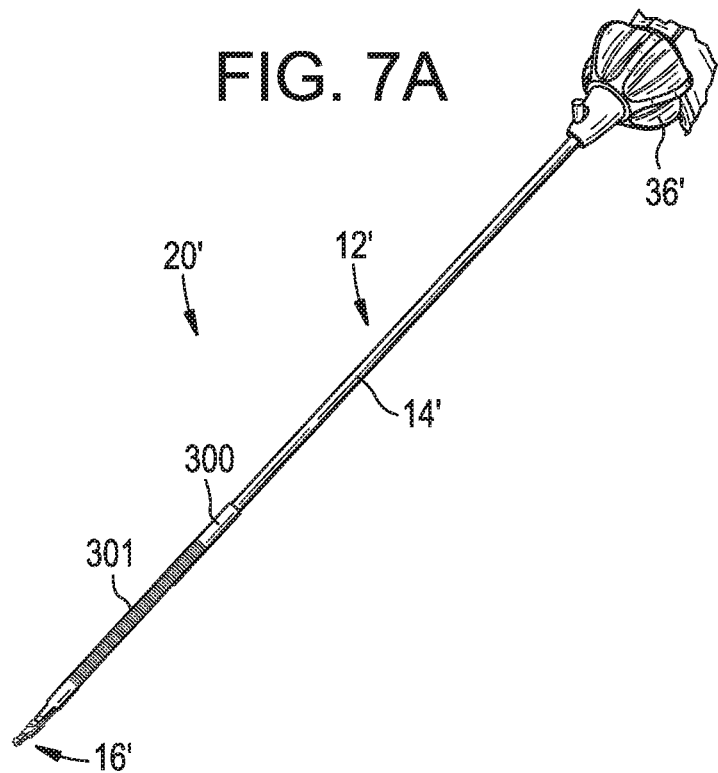
FIG. 7A is a perspective view of one embodiment of a surgical instrument including a wound protector in a distal position.
Figure 7B:
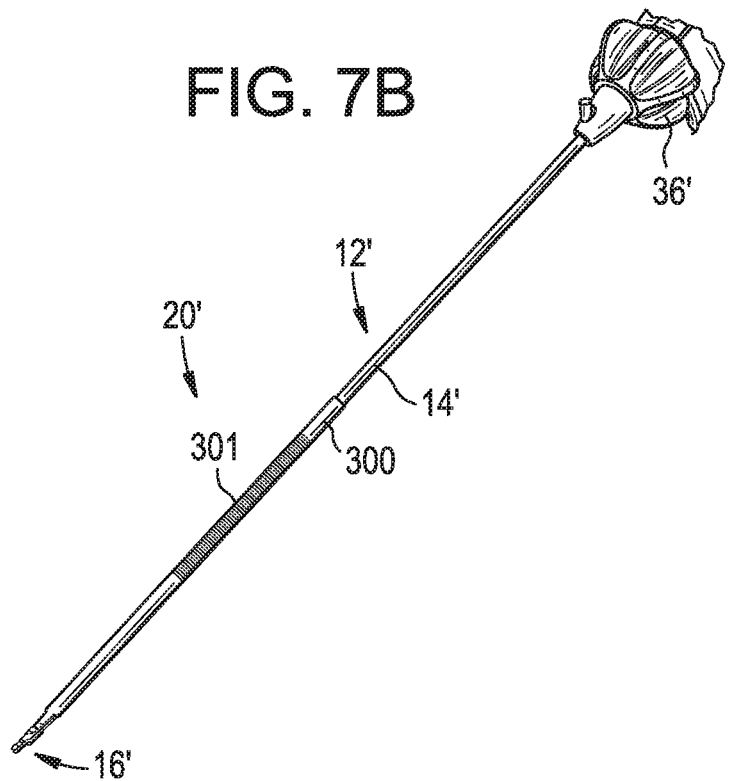
FIG. 7B is a perspective view of the surgical instrument of FIG. 7A with the wound protector in a proximal position.
Figure 7C:
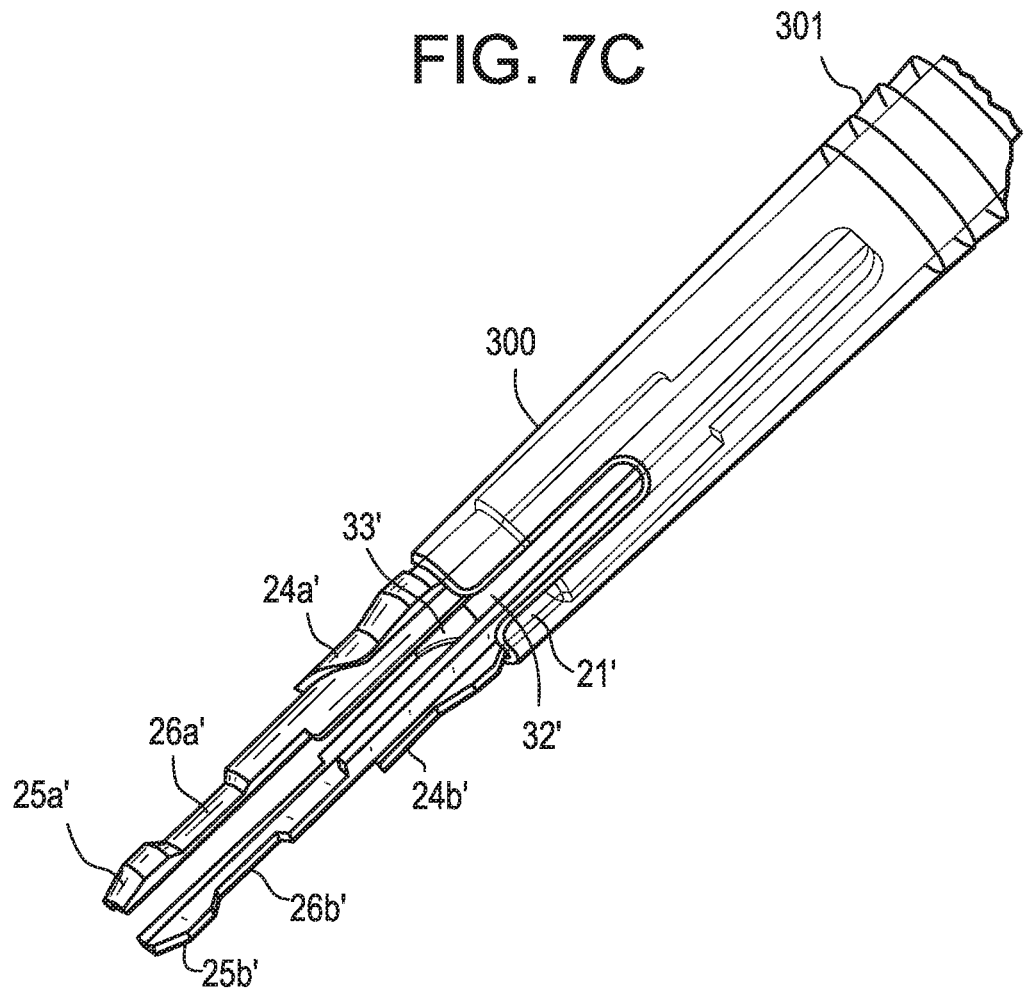
FIG. 7C is a detail view of a distal end of the instrument of FIG. 7A.

As noted above, the inner shaft can be axially slidable relative to the arms 24a, 24b, 25a, 25b between a first position, in which the inner shaft is extended distally and medial deflection of the arms is prevented (as shown in FIG. 2), and an unlocked position, in which the inner shaft is retracted proximally and medial deflection of the arms is permitted (as shown in FIG. 7C). The inner shaft 32 and intermediate shaft arms 25a, 25b can slide independently relative to the outer shaft 14 and its outer shaft arms 24a, 24b. Further, distal ends of the intermediate shaft arms 25a, 25b and distal ends of the outer shaft arms 24a, 24b can include tapered distal facing surfaces to facilitate passing through an incision and/or mating with an end effector. An end effector can be coupled to the distal end of the device 20 in vivo or ex vivo. The end effector can be coupled in a variety of ways, for example by using a loading device, as described below. In such embodiments, the loading device can hold an end effector to be attached to the distal end of the device. Use of such a device is only one possible method for associating an end effector with the device 20, however, a number of other possible methods also exist. More information on the workings of a mechanism similar to the attachment mechanism 18 can be found in U.S. Pat. Pub. No. 2011/0087267, entitled "Method for Exchanging End Effectors In Vivo," which is hereby incorporated by reference in its entirety.

The inner shaft 32, intermediate shaft 35, and outer shaft 14 can have a variety of shapes and sizes and can be made from a variety of materials, depending at least in part on the procedure being performed, the size and type of incisions and ports being used, and the other instruments, devices, and end effectors with which the device is being used. Preferred materials for forming the shafts can allow the shafts to have a degree of flexibility, and can include a variety of materials known to a person skilled in the art. The shafts are shown as being generally cylindrical, although it can take the form of a number of other shapes. Although sizes of the shafts, such as their diameter and length, can depend on the other components with which they are used and the procedure in which they are used, generally a diameter of the outer shaft 14 can be in a range of about 1 millimeter to about 10 millimeters, and in one embodiment the diameter can be about 3 millimeters, and generally a length of the outer shaft 14 can be in a range of about 50 millimeters to about 300 millimeters, more specifically in a range of about 200 millimeters to about 300 millimeters, and in one embodiment the length can be about 230 millimeters. The sizes of the intermediate shaft 35 and inner shaft 32 can vary accordingly to interact with the outer shaft 14 in the manner described herein.

Figure 3:
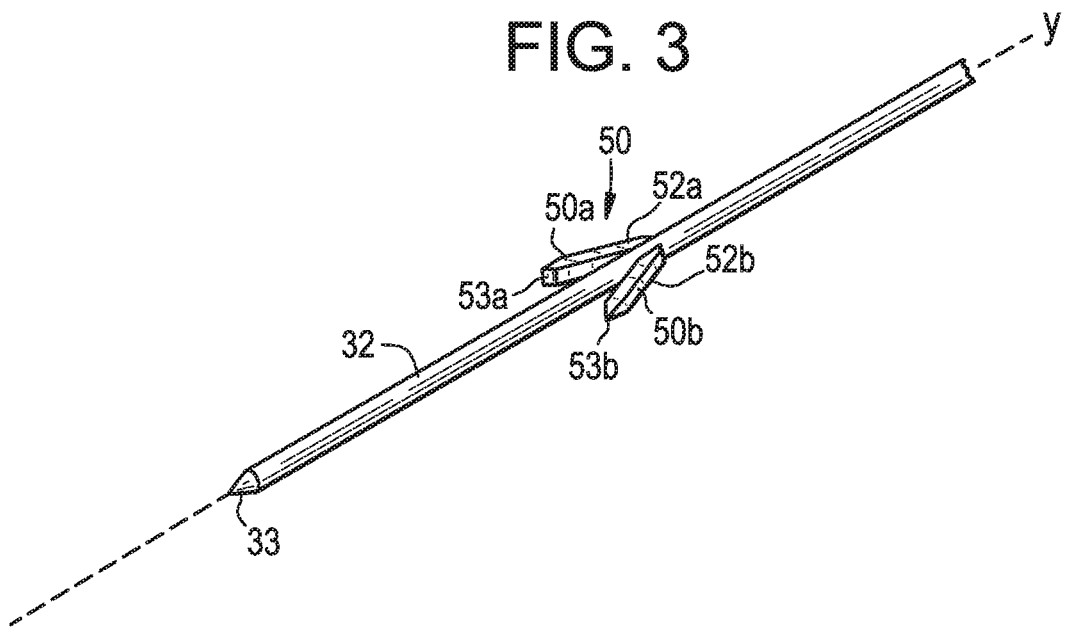
FIG. 3 is a perspective view of an inner shaft of the instrument of FIG. 1.

As shown in FIG. 3, the inner shaft 32 can include a pointed distal tip 33. The inner shaft 32 can be used to form punctures in tissue and can further be used to lock an end effector onto the distal end of the device 20. The inner shaft 32 can also have a stop guard 50 coupled thereto. The stop guard 50 can allow the pointed tip 33 to puncture tissue but prevent the pointed tip of the inner shaft 32 from advancing distally beyond a desired amount, which could possibly cause unintended damage to surrounding tissue. The stop guard 50 can have a variety of configurations and, in some embodiments, can include at least one retractable wing configured to both extend radially outward through a sidewall opening of the outer shaft and/or intermediate shaft and retract radially inward towards the inner shaft such that the retractable wing is disposed within a diameter of the outer shaft. In one embodiment, the stop guard 50 can include two retractable wings 50a, 50b. The wings 50a, 50b can be disposed on opposite sides of the inner shaft 32 from one another. The wings 50a, 50b of the stop guard 50 can be configured to extend radially outward through sidewall openings 15a, 15b of the outer shaft (see FIG. 5C). The stop guard 50 can have a fully retracted position in which an outer-most radius of the stop guard 50 is greater than a radius of the intermediate shaft 35 but less than a radius of the outer shaft 14.

In one embodiment, the stop guard 50 can be sloped, forming an acute angle with a longitudinal axis y of the inner shaft 32 in a distal-facing direction. The wings 50a, 50b can have a sloped external or proximal-facing surface 52a, 52b that forms an acute angle with the longitudinal axis y of the shaft 32 when viewed from the distal end of the shaft. Further, the wings 50a, 50b can include a distal facing surface 53a, 53b that can make contact with an external object, such as a tissue surface being penetrated, when the inner shaft 32 is advanced distally. The stop guard 50 can be coupled to the inner shaft 32 at a particular distance from the pointed distal tip 33. In one embodiment, the stop guard 50 can be positioned at a distance from the distal tip 33 that is approximately equal to the thickness of the tissue to be pierced (e.g., the thickness of the abdominal wall).

Figure 4:
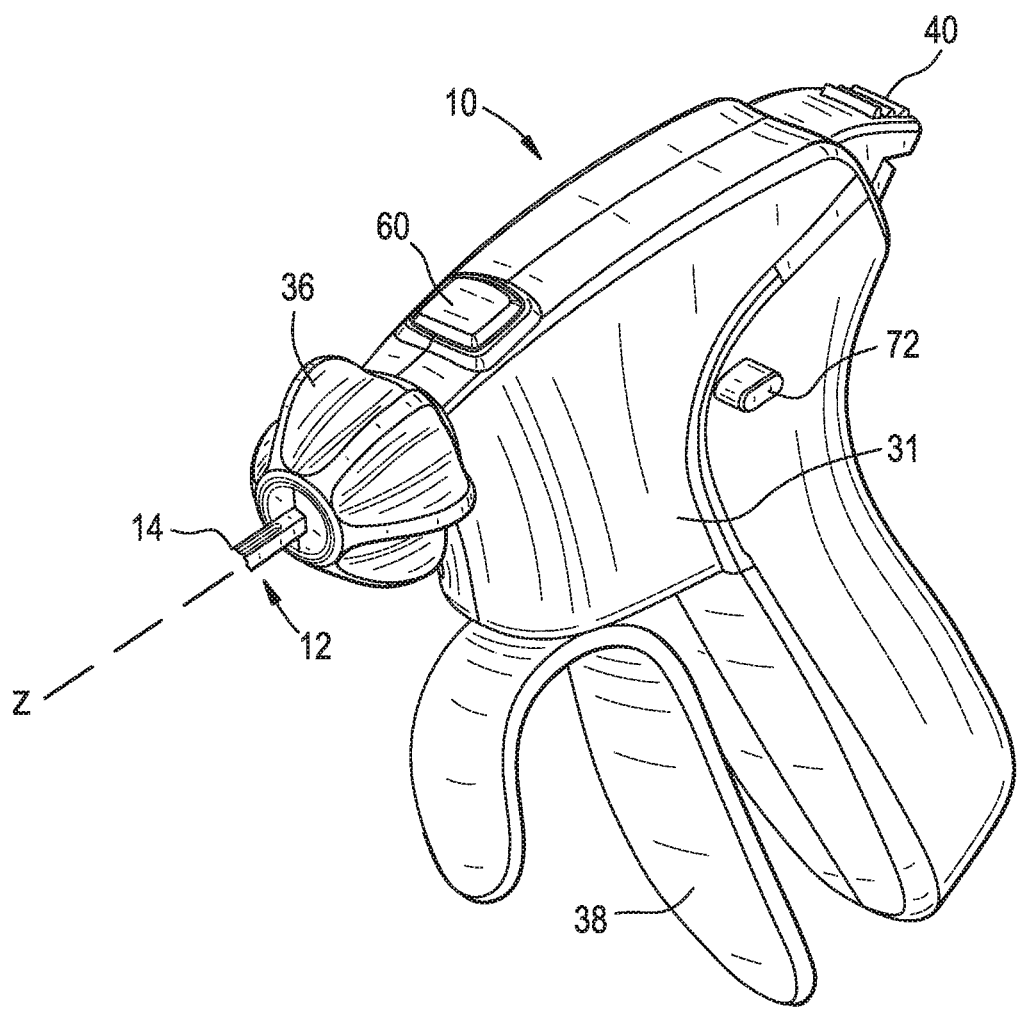
FIG. 4 is a detail view of an actuator of the instrument of FIG. 1.

FIG. 4 illustrates one embodiment of the actuator 10 that can be used with the instrument 20. The actuator 10 can include a base 31 and a knob 36. The knob 36 can rotate the attachment mechanism 18 disposed at the distal end 16 of the elongate shaft 12 about a longitudinal axis z of the elongate shaft 12, which, in turn, can rotate an attached end effector (not shown). The trigger 38 can pivot relative to the base 31 to cause axial movement of the intermediate shaft 35 relative to the outer shaft 14. In one embodiment, this movement can be transferred into the end effector to control opening and closing of jaws of an attached end effector (not shown). In other embodiments, however, this movement can be transferred into other actuation of an end effector (e.g., in cases where the end effector does not include movable jaws). A button 40, or other actuating mechanism, can control axial movement of the inner shaft 32 relative to the outer shaft 14 and intermediate shaft 35. For example, depressing the button 40 relative to the base 31 can advance the inner shaft 32 distally to the position shown in FIG. 2, which can also result in the wings 50a, 50b of the stop guard 50 being extended radially outward through the sidewall openings 15a, 15b. Conversely, releasing the button 40 can retract the inner shaft 32 proximally to the position shown in FIG. 7C, which can also result in the wings 50a, 50b of the stop guard 50 being retracted radially inward into the outer shaft 14. The lock 72 can include a button that, when depressed towards the base 31, can maintain the inner shaft 32 in a distally extended and locked position where the wings are radially extended outward from the outer shaft 14. An additional button 60 can release the elongate shaft 12 from the actuator 10 so that its various components (e.g., outer shaft 14, inner shaft 32, intermediate shaft 35) can be removed, replaced, cleaned, etc. Further information on the actuator 10 can be found in U.S. application Ser. No. 14/836,069, filed on Aug. 26, 2015, and entitled "Surgical Device Having Actuator Biasing and Locking Features," which is hereby incorporated by reference in its entirety.

Figure 5A:
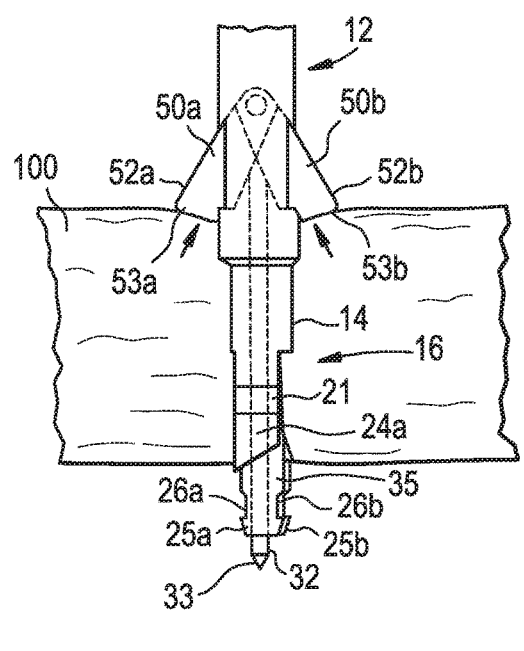
FIG. 5A is a side view of one embodiment of a surgical instrument having a stop guard advancing through tissue.
Figure 5B:
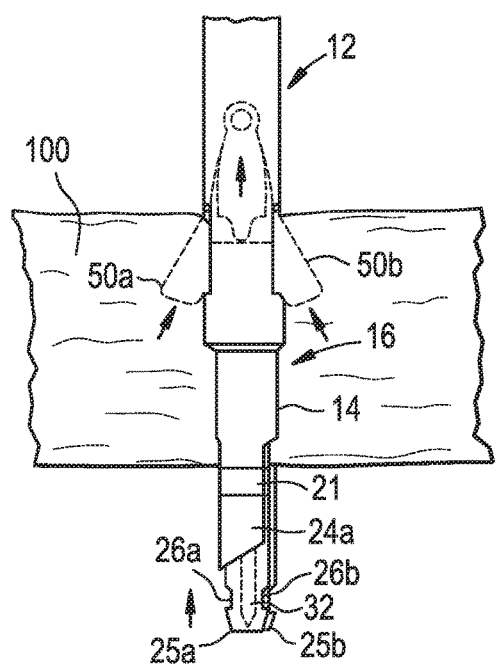
FIG. 5B is a side view of the instrument of FIG. 5A upon contact with tissue that causes the stop guard to retract radially inward and an obturator to retract proximally.
Figure 5C:
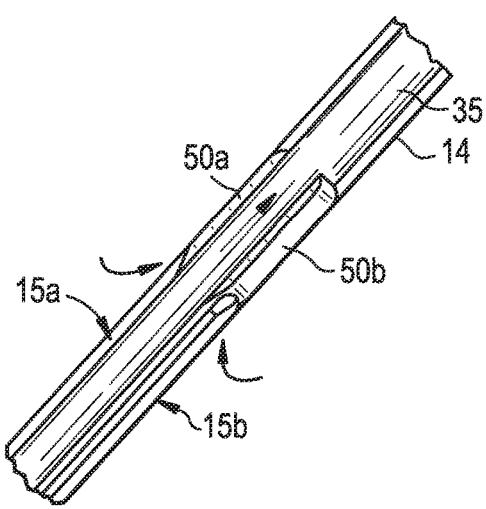
FIG. 5C is a perspective view of an inner shaft of the instrument of FIG. 5A with the stop guard retracting radially inward.

FIGS. 5A-5C illustrate an exemplary method for piercing tissue using a device including a stop guard. The method can include advancing the pointed distal tip 33 of the inner shaft 32, when in the configuration shown in FIG. 2, distally into tissue to pierce it. When the inner shaft 32 is advanced distally, the arms 25a, 25b, 24a, 24b can be locked against radially-inward movement and the wings 50a, 50b can be extended radially outward and advanced distally within the sidewall openings 15a, 15b. The wings 50a, 50b can be configured to move between a first position shown in FIG. 5A, in which the wings 50a, 50b extend through the sidewall openings 15a, 15b and the pointed distal end 33 of the inner shaft 32 extends distally beyond a distal end of the outer shaft 14, and a second position shown in FIG. 5B, in which the wings 50a, 50b are retracted towards the inner shaft 32. As the device 20 is advanced into tissue by a user, the wings 50a, 50b can contact external tissue 100 with the distal facing surfaces 53a, 53b, as shown in FIG. 5A. Force imparted onto the wings 50a, 50b from the external tissue 100 can cause the pointed distal end 33 of the inner shaft 32 to be retracted proximally. This proximal retraction can move the pointed distal end 33 towards a distal end of the intermediate shaft 35 and/or outer shaft 14. In some embodiments, the distal end 33 can be retracted proximally, such that it is disposed within the inner lumen of the intermediate shaft 35, as shown in FIG. 5B. Alternatively, or additionally, the distal end 33 can be retracted such that it is disposed within the inner lumen of the outer shaft 14. The proximal movement of the inner shaft 32 also moves the wings 50a, 50b proximally in the slots 15a, 15b. When the wings 50a, 50b reach the proximal end of the slots 15a, 15b, they can retract radially inward, as shown in FIGS. 5B and 5C. In some embodiments, when the wings 50a, 50b retract radially inward, a radius of the stop guard 50 can be less than a radius of the outer shaft 14 and greater than a radius of the intermediate shaft 35, as shown in FIG. 5C.

Once the distal tip 33 of the inner shaft 32 is retracted proximally into the inner lumen of the intermediate shaft 35 and/or outer shaft 14, the device 20 can be further advanced distally into tissue. In some embodiments, the device 20 can be advanced far enough into a patient's body that the sidewall openings 15a, 15b, from which the stop guard 50 extends, are positioned within the patient's body distally of the punctured tissue. Note that there is no resistance to advancing the device in this manner because the stop guard 50 is in a retracted configuration in which the wings 50a, 50b or other structures of the stop guard 50 are contained within the outer shaft 14.

Once positioned within a patient's body, an end effector can be coupled to a distal end of the device 20. To attach an end effector to the distal end of the device 20, the inner shaft 32 can first be refracted, as shown in FIG. 5C, if it is not already in this position (as noted above). Moving the inner shaft 32 out of the gap between the outer shaft arms 24a, 24b and/or intermediate shaft arms 25a, 25b can allow the arms to deflect radially inward as the clevis-like attachment mechanism 18 of the device 20 is inserted into a socket formed in an end effector. After the end effector is positioned correctly with respect to the attachment mechanism 18, the inner shaft 32 can be advanced distally to prevent radially-inward deflection of the outer shaft arms 24a, 24b and/or the intermediate shaft arms 25a, 25b, such that the end effector cannot be separated from the attachment mechanism 18. Distal advancement of the inner shaft 32 can also cause the wings 50a, 50b of the stop guard 50 to advance distally and extend radially outward from the sidewall openings 15a, 15b. In this configuration, wherein the stop guard wings 50a, 50b are deployed inside a patient's body, the stop guard 50 can prevent inadvertent withdrawal of the device 20 but providing resistance to removal once the stop guard wings contact the punctured tissue. Unlike when advancing the device 20 distally through tissue, however, the sloped configuration of the wings 50a, 50b can allow for removal of the device 20 if necessary (e.g., in an emergency). In one embodiment, for example, about 4 lbs of resistive force are provided against withdrawal of the device 20 from the body by the sloped surfaces 52a, 52b of the wings 50a, 50b. This is in comparison to, for example, about 1 lb of force that is required for a similar instrument without a stop guard 50.

In embodiments in which the end effector is attached in vivo, the end effector can be introduced into the body using a loading device that is introduced through a trocar or other suitably sized opening or port. Once a procedure is complete, the end effector can be recaptured by the loading device and decoupled from the device 20 by retracting the inner shaft 32 proximally to free the clevis-like attachment mechanism 18 to deflect radially inward and release the end effector. Proximally retracting the inner shaft 32 can also retract the stop guard wings 50a, 50b radially inward within the outer shaft 14, thereby allowing the device 20 to be removed from the patient's body without experiencing increased levels of resistance from the stop guard 50.

FIG. 6A illustrates one exemplary embodiment of the method described generally above. As shown in FIG. 6A, a puncture 101 can be created in an abdominal wall 100 using the device 20. More particularly, the puncture 101 can be created using the pointed distal tip 33 of the inner shaft 32 of the instrument 20 by passing the inner shaft distally through the lumen of the outer shaft 14 and/or intermediate shaft 35 until it is extended distally beyond the distal end of the outer shaft and/or intermediate shaft. When the inner shaft 32 is advanced distally to puncture tissue, a stop guard 50 can extend radially outward from the outer shaft 14 and can contact the tissue 100. Force exerted on the stop guard 50 by the tissue 100 can cause the inner shaft 32 to retract proximally such that a distal end of the inner shaft 32 is disposed within an inner lumen of the intermediate shaft 35 and/or outer shaft 14 (as discussed above with respect to FIGS. 5A-5C). This retraction can also cause the stop guard 50 to retract radially inward into the inner lumen of the outer shaft 14. In this configuration, the device 20 can be further advanced through the abdominal wall 100 to the position shown in FIG. 6A. No resistance is encountered due to the stop guard because it is in a retracted configuration that does not extend from the outer shaft 14. Further, the attachment mechanism 18 is in a configuration that is ready to accept any of a variety of end effectors for coupling thereto. Finally, as shown the distal end of the device 20 and the elongate shaft 12 can pass through the abdominal wall 100 without utilizing a trocar or other access port, as the resilient abdominal wall 100 can seal directly against the shaft 12 to maintain pneumoperitoneum during a procedure.

In the embodiment illustrated in FIG. 6A, the end effector 105 is inserted into the abdominal cavity using a loading device 200. The loading device 200 can be inserted into the patient's body in a variety of manners, but typically an incision 103 can be created in a patient's body and a trocar can be positioned within the incision to allow the loader 200 to pass into the abdominal cavity. The end effector 105 can be attached to the instrument 20 in a number of different ways either outside or inside of a subject's body. For example, in some embodiments a distal end of the device 20 can be inserted through a trocar such that it exits the patient's body, and the end effector can be attached thereto before the device 20 is pulled back through the trocar into the abdominal cavity. In other embodiments, however, the end effector 105 can be configured to be attached to the device 20 within a patient's body or in vivo, e.g., within a body cavity such as the abdominal cavity, and to be removed and replaced within the patient's body.

The type of end effector that can be employed is not particularly limited. In general, end effectors can include jaws or they can be non-jawed end effectors. A variety of different end effectors 105 can be attached and detached from the instrument 20. In some embodiments, the instrument 20 can be operated by the actuator 10 to cause the end effector 105 to grasp tissue or lock its jaws. In other embodiments, operation of the actuator 10 can cause the end effector to perform other tasks, such as cutting, energy delivery, etc.

As shown in FIG. 6B, the end effector 105 can be loaded onto the device 20 using a loading device 200. To load the end effector 105 onto the device 20, the end effector can be aligned with a longitudinal axis of the elongate shaft 12 (i.e., longitudinal axis z). Further, the inner shaft 32 can be retracted proximally (if not already in such a configuration) to ensure that the intermediate shaft arms 25a, 25b and outer shaft arms 24a, 24b can deflect radially inward.

In such a configuration, the device 20 can be advanced distally such that the attachment mechanism 18 (including the intermediate shaft arms 25a, 25b and outer shaft arms 24a, 24b) are inserted into a mating socket formed in the end effector 105. Ridges or annular protrusions formed on the mating socket sidewalls can slide over the attachment mechanism 18, deflecting the intermediate shaft arms 25a, 25b and outer shaft arms 24a, 24b radially inward until such ridges or protrusions are seated within grooves or notches 21, 26a, 26b formed in the arms 24a, 24b, 25a, 25b. A user can experience tactile or audible feedback when the correct position is reached. In this configuration, the end effector 105 is coupled to the device 20, but can be pulled free in the same manner it was attached due to the deflection of the arms 24a, 24b, 25a, 25b. To lock the end effector 105 onto the device 20, the inner shaft 32 can be advanced distally such that the inner shaft 32 fills the gap between the arms 24a, 24b, 25a, 25b and prevents any radial inward deflection thereof. Note that this distal advancement of the inner shaft 32 can also cause the stop guard 50 to be advanced distally and extended radially outward from the outer shaft 14, thereby providing a stop to prevent inadvertent withdrawal of the device while coupled to an end effector. A surgeon or other user can then draw the device 20 away from the loading device 200, as shown in FIG. 6D, and carry out the surgical procedure using the actuator 10 to effect movement of the end effector jaws or other tool.

After the function of the end effector 105 is performed, the instrument 20 can be detached from the end effector 105 and removed from the surgical site using the reverse of the procedure detailed above. For example, the inner shaft 32 can be retracted proximally to allow the end effector 105 to be pulled away from the device 20 using the loading device 200. Moreover, when the inner shaft 32 is retracted proximally to allow decoupling of the end effector 105, the stop guard 50 can be retracted radially inward into the outer shaft 14. This can allow the instrument 20 to be removed from the tissue through the puncture 101 without experiencing resistance from the stop guard 50. The loading device 200 can subsequently be reattached to the end effector 105 to remove it from the patient's body through the trocar or other port used to introduce the loading device into the patient's body. If further procedures are necessary, a new or different end effector can be attached to the loading device 200 and coupled to the device 20 in the manner described above, or the device can be removed from the patient's body if the procedure is concluded.

In addition to the stop guard 50 described above, other features can also be included in surgical devices to further protect tissue and prevent inadvertent withdrawal of the device from the patient's body. For example, in the embodiment shown in FIGS. 7A-7D, a wound protector 300 can be included on the instrument 20'. The wound protector 300 can prevent damage to punctured tissue and can minimize friction and drag forces on the instrument when it is moved proximally and distally in tissue. In other words, the wound protector 300 can act similar to a trocar, which maintains an opening formed in tissue and allows other instruments to be passed through the tissue. As shown in the figures, the wound protector 300 can be a cylindrical sleeve slidably disposed over the outer shaft 14'. The wound protector 300 can be smooth or ridged on an exterior surface thereof. Ridges 301 on the exterior surface of the wound protector 300 can allow the wound protector 300 to better engage with tissue and prevent movement of the wound protector relative to the punctured tissue.

The wound protector 300 can also function to prevent inadvertent withdrawal of the instrument 20' from the patient's body. For example, the wound protector 300 can be configured such that it binds against a distal end of the outer shaft 14'. In such an embodiment, a user withdrawing the instrument 20' proximally from the configuration shown in FIG. 7B would experience substantially no friction until the wound protector 300 reached the position shown in FIG. 7A. At that point, the wound protector 300 can stop sliding over the outer shaft 14', which can result in the user having to overcome increased resistance to further proximal withdrawal. This is because the wound protector does not move relative to the tissue nearly as easily as it moves over the outer shaft 14', especially if ridges 301 or other gripping features are employed on an outer surface of the wound protector 300.

Figure 7D:
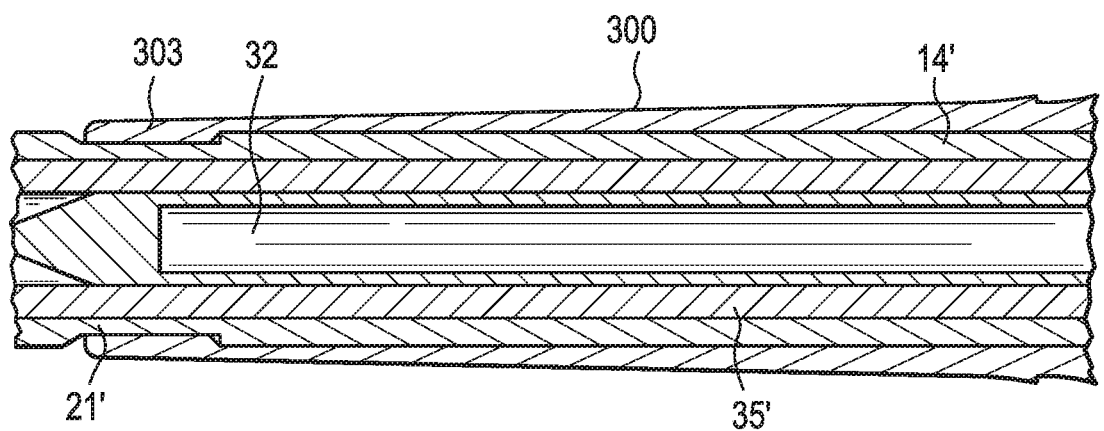
FIG. 7D is a side cross-sectional view of a distal end of the instrument of FIG. 7A.

In some embodiments, the wound protector 300 can include an annular ridge or protrusion 303 formed on an inner sidewall thereof near its distal end. This annular ridge or protrusion 303 can be configured to be seated within the circumferential groove 21' of the outer shaft 14' when the wound protector 300 is at a distal-most position relative to the outer shaft, as shown in FIGS. 7C and 7D. The mating of the protrusion 303 and groove 21' can serve to define the distal-most position of the wound protector 300 that helps prevent inadvertent withdrawal of the device 20.

Positioning the wound protector at the distal position shown in FIGS. 7C and 7D can also help to protect the clevis-like attachment mechanism 18' disposed at the distal end of the device 20'. It should be appreciated that, at certain sizes, the opposed intermediate shaft arms 25a', 25b' and outer shaft arms 24a', 24b' can be quite small and thin. There is a risk that these arms can become permanently bent or otherwise deformed if, for example, an end effector 105 is not correctly aligned during coupling (e.g., if only one of the arms 25a', 25b' enters the mating socket of the end effector while the other arm remains outside the socket, the arms can be bent away from one another). It is also possible that tissue or other nearby structures can catch one of the arms 24a', 24b', 25a', 25b' during insertion and/or withdrawal of the instrument. Placing the wound protector 300 in the position shown in FIGS. 7C and 7D can provide a sheath around the arms that reinforces them and prevents excessive outward radial deflection.

Figure 8:
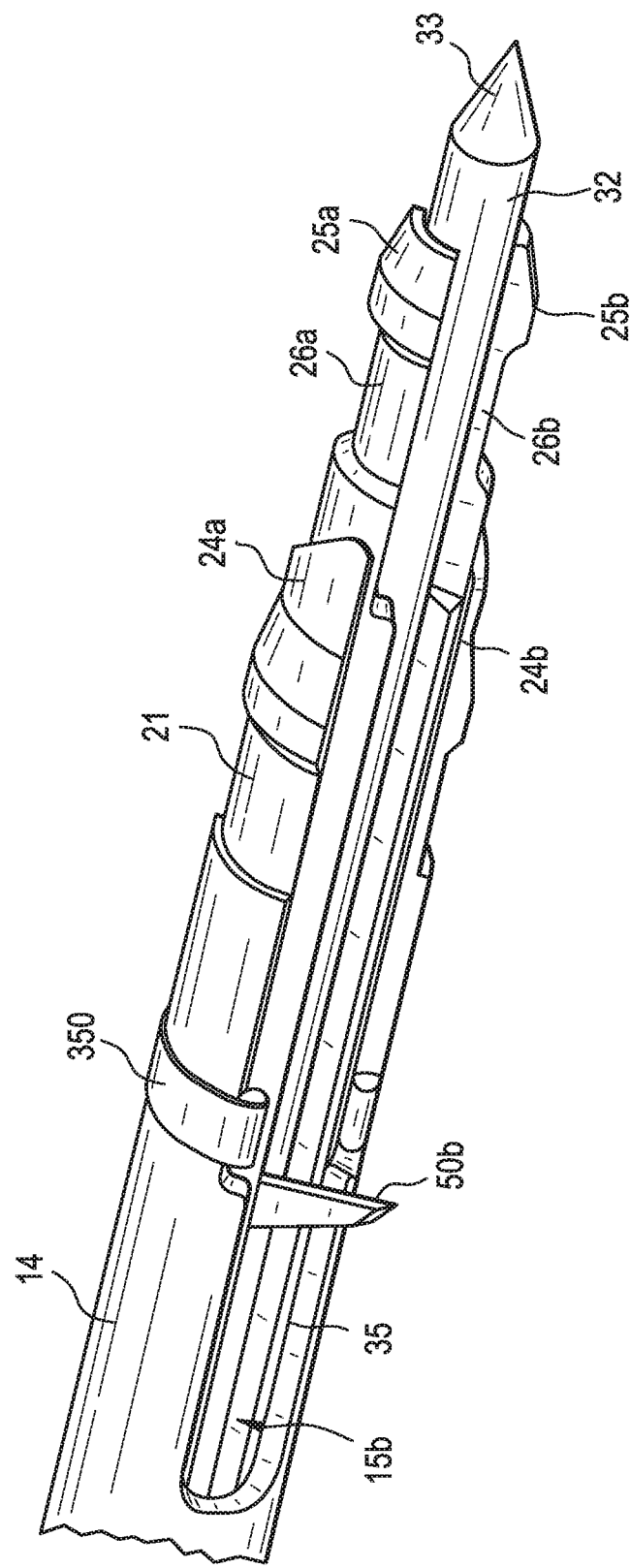
FIG. 8 is a perspective view of one embodiment of a surgical instrument including a supporting spring clip.

The wound protector 300 is not the only way in which support for the clevis-like attachment mechanism and its arms can be provided. FIG. 8, for example, illustrates another embodiment in which the arms are protected using a spring clip 350 disposed around a distal portion of the device. The spring clip 350, such as a c-shaped snap ring, can engage the arms 24a, 24b of the outer shaft 14 to provide support and prevent bending or damage to the arms 24a, 24b, 25a, 25b. The spring clip 350 can be made of material that is less flexible than the material of the arms, but can also be biased to tension the arms 24a, 24b, 25a, 25b while still allowing the above-described functionality.

In still other embodiments, additional features can be provided to prevent inadvertent withdrawal of a device during use. For example, in some embodiments an end effector can include a flared proximal-facing (when coupled to the instrument, e.g., as shown in FIG. 6D) profile that can provide increasing resistance to removal similar to the sloped stop guard wings 50a, 50b. Similar to the sloped wings, a flared shape would prevent inadvertent withdrawal of the instrument, while still allowing for removal if needed (e.g., in an emergency). In other embodiments, a luer fitting can be included on the elongate shaft 12 and/or an end effector 105 to provide a similar flared shape that can prevent inadvertent withdrawal of the device during use. By way of example, a luer fitting having an inner diameter that matches a diameter of the shaft 12 can be slid over the shaft with its taper facing proximally to provide a slidable stop that can prevent inadvertent extraction of the shaft 12 from the abdomen or other surgical site.

Any of the components and devices known in the art and/or described herein can be provided as part of a kit including an elongate shaft and a plurality of end effectors each configured to be removably and replaceably mated to a distal end of the surgical instrument's elongate shaft, as discussed above. The kit can include one or more percutaneous instruments having a handle and a shaft, one or more end effectors, and one or more obturators to selectively lock and unlock end effector(s) from the instrument(s). The end effectors provided in the kit can perform different functions, including but not limited to the functions described herein, and/or can be included together in a single kit to perform a particular function, such as a kit specifically tailored for stretching and stapling tissue. Further, one or more trocars, ports, loaders, and viewing instruments, such as endoscopes or cameras, can be provided to assist in introducing the instruments and end effectors to the surgical site.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument, comprising:
   an outer shaft having an inner lumen and at least one opening extending through an outer sidewall of the outer shaft;
   an inner shaft disposed within the inner lumen of the outer shaft and configured to translate relative to the outer shaft along a longitudinal axis thereof, the inner shaft including a distal end configured to puncture tissue;
   a stop guard coupled to the inner shaft, the stop guard having at least one retractable wing configured to both extend radially outward through the at least one opening of the outer shaft and retract radially inward towards the inner shaft such that the retractable wing is disposed within a diameter of the outer shaft; and
   an intermediate shaft having an inner lumen and at least one opening extending through an outer sidewall of the intermediate shaft, the intermediate shaft being disposed between the outer shaft and the inner shaft and configured to translate relative to the outer shaft along a longitudinal axis thereof, the intermediate shaft being further configured to translate to a position at which the at least one opening of the intermediate shaft is aligned along at least a portion of its length with the at least one opening of the outer shaft and a distal end of the intermediate shaft extends distally beyond the distal end of the outer shaft;
   wherein, when the at least one retractable wing is extending radially outward through the at least one opening of the outer shaft, the at least one retractable wing is configured to retract radially inward towards the inner shaft in response to the at least one retractable wing coming into contact with an external object as the instrument is advanced distally into tissue, the radially inward retraction of the at least one retractable wing resulting in the distal end of the inner shaft retracting proximally towards the distal end of the outer shaft.

2. The instrument of claim 1, wherein, upon contact with the external object by the at least one retractable wing, the distal end of the inner shaft retracts proximally towards the distal end of the outer shaft such that the distal end of the inner shaft is disposed within the inner lumen of the outer shaft.

3. The instrument of claim 1, wherein, upon contact with the external object by the at least one retractable wing, the distal end of the inner shaft retracts proximally towards the distal end of the intermediate shaft such that the distal end of the inner shaft is disposed within the inner lumen of the intermediate shaft.

4. The instrument of claim 1, wherein each of the intermediate and outer shafts further comprises first and second deflectable arms.

5. The instrument of claim 4, further comprising an end effector configured to be coupled to at least one of the distal end of the intermediate shaft and the distal end of the outer shaft by the inner shaft extending the first and second deflectable arms of the intermediate shaft radially outward towards sidewalls of the end effector.

6. The instrument of claim 5, wherein the at least one retractable wing of the stop guard is configured to extend radially outward through the at least one opening of the outer shaft when the end effector is coupled to at least one of the distal end of the intermediate shaft and the distal end of the outer shaft.

7. The instrument of claim 1, wherein the stop guard has a fully retracted position in which an outer-most radius of the stop guard is greater than a radius of the intermediate shaft but less than a radius of the outer shaft.

8. The instrument of claim 1, wherein the at least one retractable wing of the stop guard comprises a first retractable wing and a second retractable wing, the first and second retractable wings being configured to extend radially outward through first and second openings of the outer sidewall of the outer shaft, respectively, and retract radially inward towards the inner shaft such that the first and second retractable wings are disposed within a diameter of the outer shaft.

9. The instrument of claim 8, wherein the first and second retractable wings are disposed on opposite sides of the inner shaft from one another.

10. A surgical instrument, comprising:
an outer shaft having an inner lumen and at least one opening extending through an outer sidewall of the outer shaft;
an inner shaft disposed within the inner lumen of the outer shaft and configured to translate relative to the outer shaft along a longitudinal axis thereof, the inner shaft including a distal end configured to puncture tissue;
an intermediate shaft having an inner lumen and at least one opening extending through an outer sidewall of the intermediate shaft, the intermediate shaft being disposed between the outer shaft and the inner shaft and configured to translate relative to the outer shaft along a longitudinal axis thereof, the intermediate shaft further being configured to translate to a position at which the at least one opening of the intermediate shaft is aligned along at least a portion of its length with the at least one opening of the outer shaft and a distal end of the intermediate shaft extends distally beyond the distal end of the outer shaft; and
a stop guard coupled to the inner shaft, wherein the stop guard extends through the at least one opening of the outer shaft when the distal end of the inner shaft extends beyond a distal end of the outer shaft, and wherein the stop guard proximally retracts the inner shaft when the stop guard contacts tissue such that the distal end of the inner shaft is contained within the inner lumen of the outer shaft.

11. The instrument of claim 10, wherein the stop guard is configured to move between a first position, in which the stop guard extends through the at least one sidewall opening when the distal end of the inner shaft extends distally beyond a distal end of the outer shaft, and a second position, in which the stop guard is retracted towards the inner shaft such that a radius of the stop guard is less than a radius of the outer shaft when the distal end of the inner shaft is disposed within the inner lumen of the outer shaft.

12. The instrument of claim 10, wherein each of the intermediate and outer shafts further comprise first and second deflectable arms.

13. The instrument of claim 12, wherein the stop guard is configured to move to a third position, in which the stop guard extends through the at least one sidewall opening of both the intermediate shaft and the outer shaft, and the distal end of the inner shaft is disposed at or distal of the distal end of the intermediate shaft to cause the first and second deflectable arms of the intermediate shaft to extend radially outward towards sidewalls of an end effector to couple the end effector to at least one of the intermediate shaft and the outer shaft.

14. A surgical instrument, comprising:
an outer shaft having an inner lumen and at least one opening extending through an outer sidewall of the outer shaft;
an inner shaft disposed within the inner lumen of the outer shaft and configured to translate relative to the outer shaft along a longitudinal axis thereof, the inner shaft including a distal end configured to puncture tissue; and
a stop guard coupled to the inner shaft, the stop guard having at least one retractable wing configured to both extend radially outward through the at least one opening of the outer shaft and retract radially inward towards the inner shaft such that the retractable wing is disposed within a diameter of the outer shaft,
wherein, when the at least one retractable wing is extending radially outward through the at least one opening of the outer shaft, the at least one retractable wing is configured to retract radially inward towards the inner shaft in response to the at least one retractable wing coming into contact with an object external to the instrument as the instrument is advanced distally into tissue, the radially inward retraction of the at least one retractable wing resulting in the distal end of the inner shaft retracting proximally towards the distal end of the outer shaft.

15. The instrument of claim 14, wherein, upon contact with the external object by the at least one retractable wing, the distal end of the inner shaft retracts proximally towards the distal end of the outer shaft such that the distal end of the inner shaft is disposed within the inner lumen of the outer shaft.

16. The instrument of claim 14, wherein the at least one retractable wing of the stop guard comprises a first retractable wing and a second retractable wing, the first and second retractable wings being configured to extend radially outward through first and second openings of the outer sidewall of the outer shaft, respectively, and retract radially inward towards the inner shaft such that the first and second retractable wings are disposed within a diameter of the outer shaft.

17. The instrument of claim 16, wherein the first and second retractable wings are disposed on opposite sides of the inner shaft from one another.

* * * * *